(12) United States Patent
Neeman et al.

(10) Patent No.: US 7,485,181 B2
(45) Date of Patent: Feb. 3, 2009

(54) COMPOSITIONS FOR DETECTING HYALURONIDASE ACTIVITY IN SITU AND METHODS OF UTILIZING SAME

(75) Inventors: Michal Neeman, Mazkeret-Batya (IL); Liora Shiftan, Gedera (IL)

(73) Assignee: Yeda Research and Development Co. Ltd., Rechovot (IL)

( * ) Notice: Subject to any disclaimer, the term of this patent is extended or adjusted under 35 U.S.C. 154(b) by 14 days.

(21) Appl. No.: 10/959,417

(22) Filed: Oct. 7, 2004

(65) Prior Publication Data

US 2006/0078500 A1   Apr. 13, 2006

(51) Int. Cl.
*C09D 105/08* (2006.01)
*C12Q 1/34* (2006.01)
(52) U.S. Cl. .................................. 106/162.2; 435/18
(58) Field of Classification Search .................. None
See application file for complete search history.

(56) References Cited

U.S. PATENT DOCUMENTS 5,900,481 A * 5/1999 Lough et al. .............. 536/55.3
6,569,636 B2 * 5/2003 Grothaus et al. ........... 435/7.92

OTHER PUBLICATIONS

Neiminen et al. Spatial Assessment of Articular Cartilage Proteoglycans with GD-DTPA-Enhanced T1 Imaging; Magnetic Resonance in Medicine, vol. 48 (2002) pp. 640-648.*
Thierry et al. Radionucleotides-Hyaluronan-Conjugate Thromboresistant Coatings to Prevent In-Stent Restenosis; Biomaterials, vol. 25 (2004) pp. 3895-3905.*
Thierry et al. Magnetic Resonance Signal-Enhancing Self-Assembled Coating for Endovascular Devices; Polymeric Materials: Science and Engineering vol. 89 (2003) pp. 329-330.*
Casey et al, "Cell membrane glycosylation mediates the adhesion, migration, and invasion of ovarian carcinoma cells", *Clin Exp Metastasis*. 2003;20(2):143-52.
Lessan et al, "CD44 and beta1 integrin mediate ovarian carcinoma cell adhesion to peritoneal mesothelial cells", *Am J Pathol*. May 1999;154(5):1525-37.
Takahashi et al, "A fluorimetric Morgan-Elson assay method for hyaluronidase activity", *Anal Biochem*. Nov. 15, 2003;322(2):257-63.
Gouin et al, "Quantitative assays of the amount of diethylenetriaminepentaacetic acid conjugated to water-soluble polymers using isothermal titration calorimetry and colorimetry", *Bioconjug Chem*. May-Jun. 2001;12(3):372-7.
Schiffenbauer et al, "Gonadotropin stimulation of MLS human epithelial ovarian carcinoma cells augments cell adhesion mediated by CD44 and by alpha(v)-integrin", *Gynecol Oncol*. Feb. 2002;84(2):296-302.
Shiftan et al, "MRI detection of hyaluronidase secreted by ovarian carcinoma cells", Matrix Biology Institute HA 2003 Proceedings, Chapter 3 "Biodegradation" found at: http://www.matrixbiologyinstitute.org/ha03/ch3/index.htm.
Tempel et al, "Hyaluronic acid as an anti-angiogenic shield in the preovulatory rat follicle", *Biol Reprod*. Jul. 2000;63(1):134-40.

* cited by examiner

*Primary Examiner*—Jon P Weber
*Assistant Examiner*—Paul C. Martin

(57) ABSTRACT

A composition-of-matter is provided. The composition-of-matter comprising a chelator moiety-hyaluronan complex bound to a solid support. Also provided are methods of in-situ assessing hyaluronidase activity using such compositions.

26 Claims, 5 Drawing Sheets

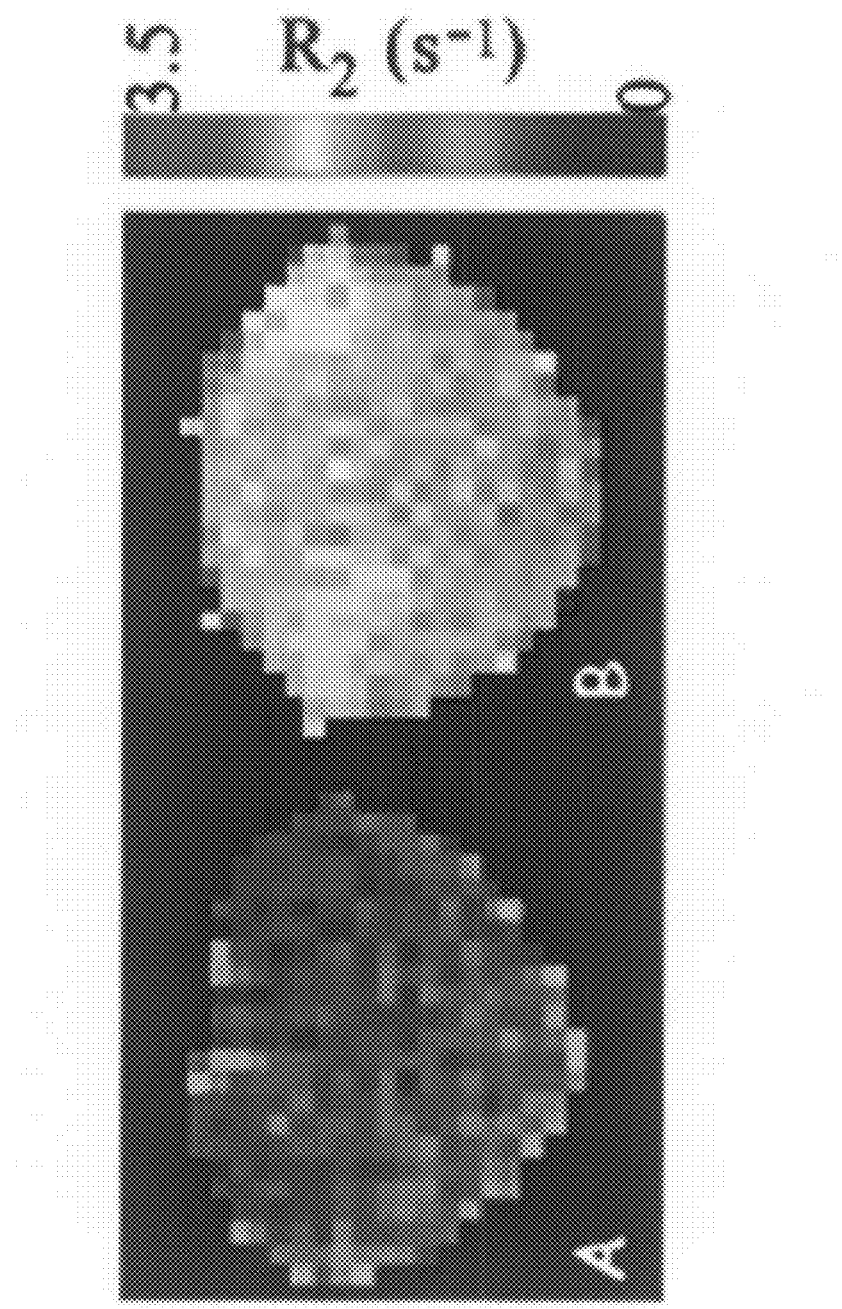
Figs. 2a-b

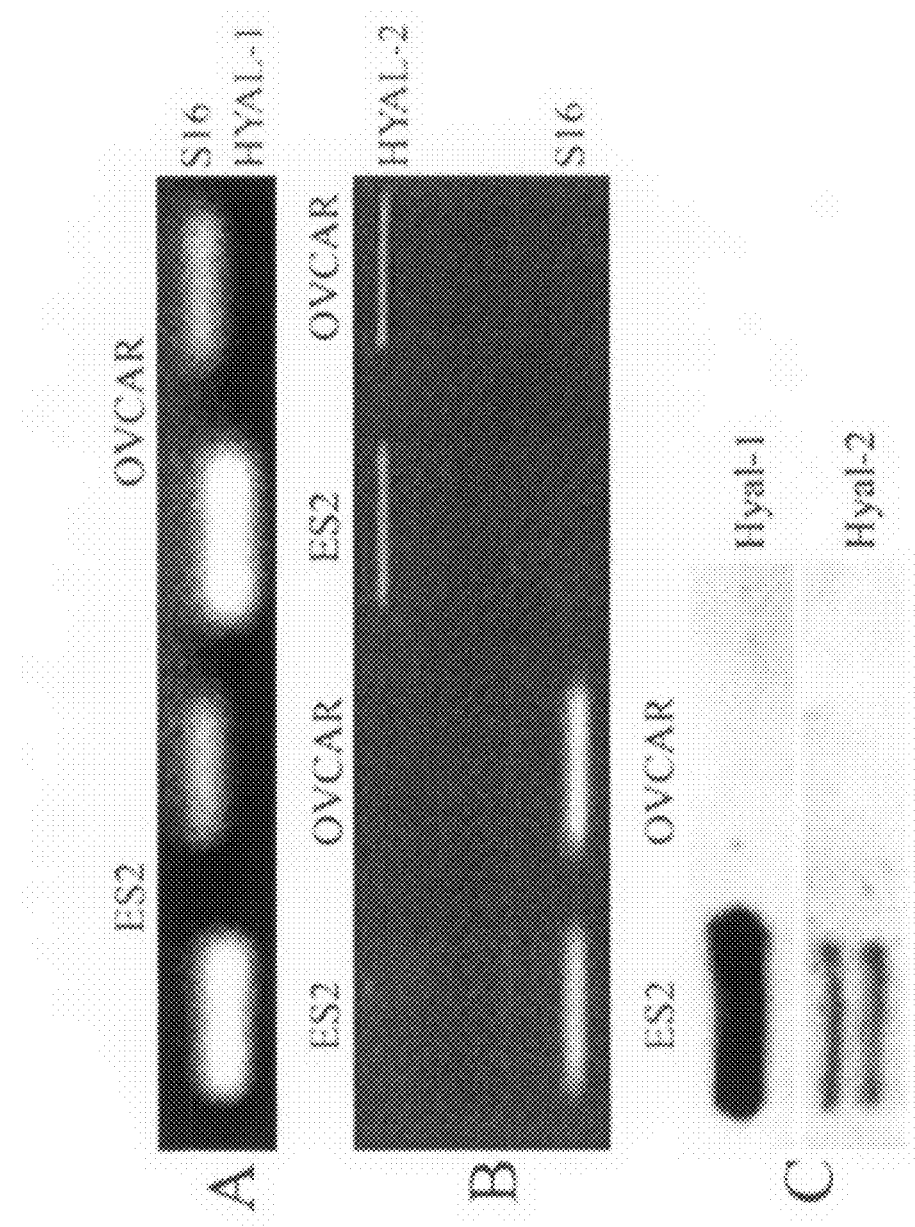
Figs. 3a-c

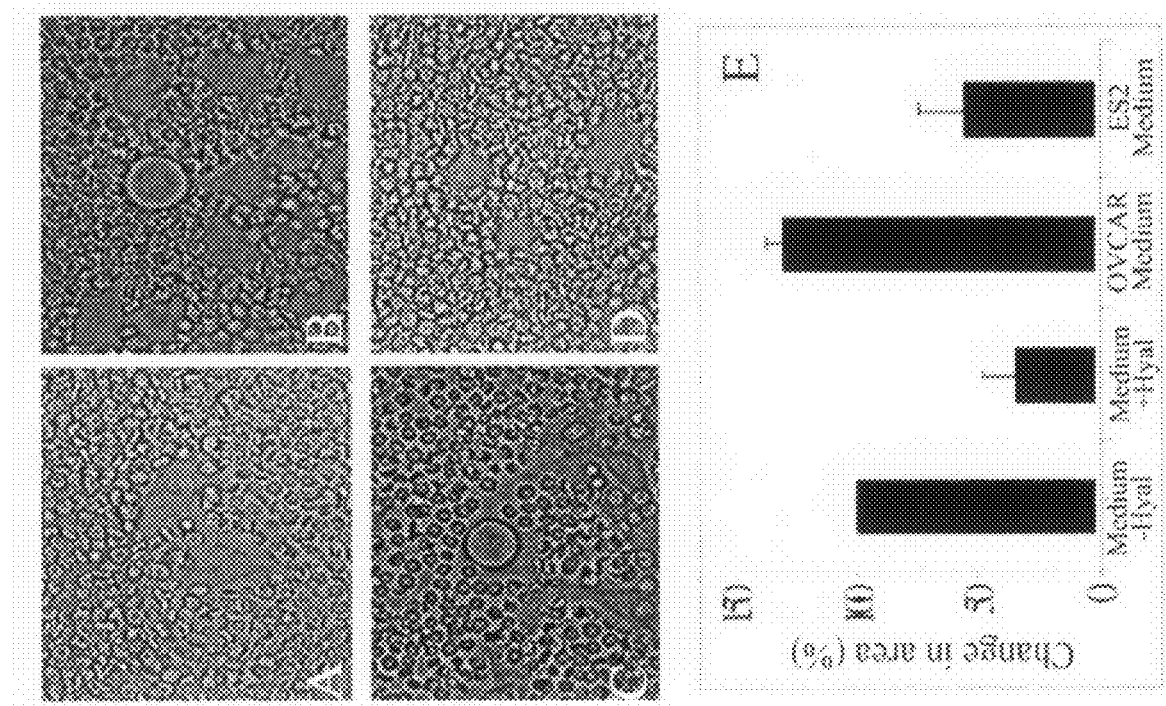
Figs. 4a-e

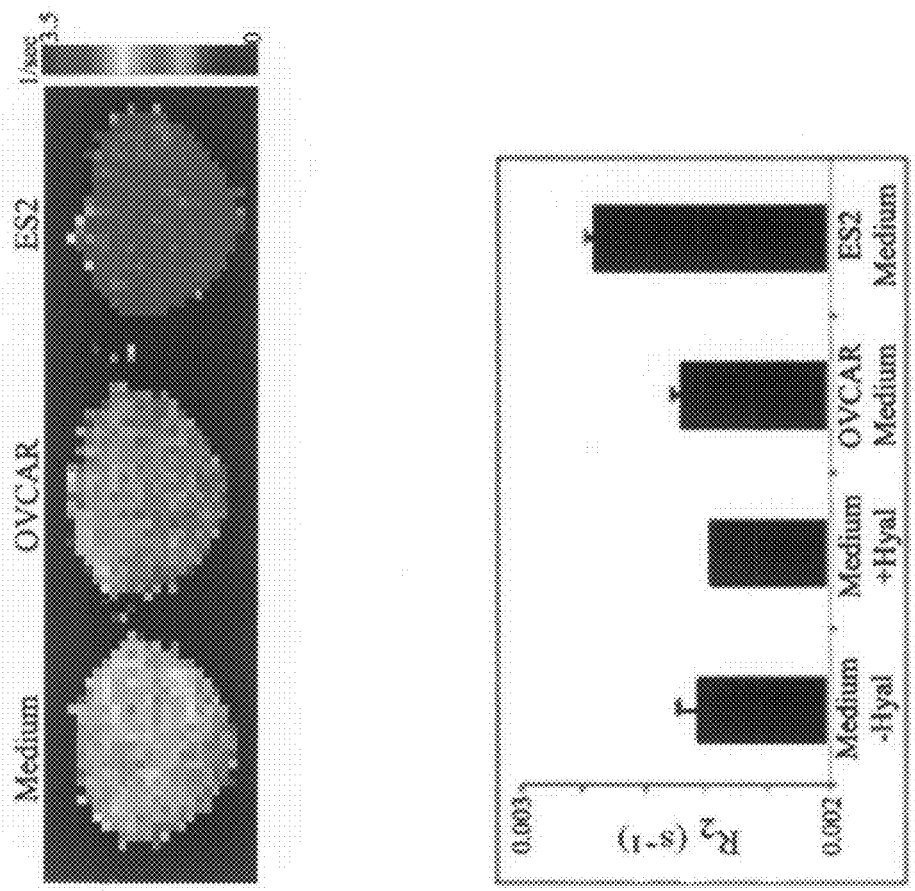
Figs. 5a-b under Contract No. R01 CA75334 awarded by the National Institute of Health. The United States government has certain rights in the invention.

COMPOSITIONS FOR DETECTING HYALURONIDASE ACTIVITY IN SITU AND METHODS OF UTILIZING SAME

STATEMENT OF GOVERNMENT INTEREST

This invention was made in part by government support under Contract No. R01 CA75334 awarded by the National Institute of Health. The United States government has certain rights in the invention.

FIELD AND BACKGROUND OF THE INVENTION

The present invention relates to compositions and methods for detecting hyaluronidase activity in situ and, more particularly, to methods of diagnosing cancer.

Hyaluronan (HA), also known as hyaluronate or hyaluronic acid, is a high molecular weight linear glycosaminoglycan, composed of repeating disaccharides of glucuronic acid and N-acetylglucosamine. HA is an important structural component of cartilage, synovial fluid, skin of vertebrates as well as of the vitreous humor of the eye (1). Hence, HA plays an important role in maintenance of intact architecture in normal tissues; it absorbs a large volume of water and creates a gel-like environment. This environment enables facilitating biological processes that require cell movement such as tissue organization and morphogenesis, wound healing, inflammation, and angiogenesis, as well as in pathological processes such as cancer metastasis.

High molecular weight HA is degraded by hyaluronidase (hyal). Low molecular weight degradation products are known to stimulate endothelial cell proliferation and to promote neovascularization, while the native high molecular weight HA is anti-angiogenic (2). Hyaluronidase was first identified in 1928 as a "spreading factor" of viral agents and was later characterized as HA-degrading enzyme and named hyaluronidase (3-5). Hyaluronidase activity is high in necrotic tumors and is elevated in the sera of cancer patients (6). Six hyal-like gene sequences, coding for ubiquitous enzymes with varying substrate specificities, were described in mammals based on their enzymatic activity and optimal pH for activity (7).

Primarily investigated hyaluronidase protein products are Hyal-1, Hyal-2 and PH-20. Hyal-1, the plasma hyaluronidase is a 57-kDa protein composed of a single polypeptide chain of 49 kDa with approximately 8 kDa of post-translational glycosylation. Hyal-1 is a lysosomal enzyme that can cleave HA to small tetra-and-disaccharides (8). Hyal-1 is found at high concentrations in the urine and has approximately 40% identity to the enzyme PH-20 found mainly in sperm (7). Hyal-1 is also known as LUCA-1 (LUng CAncer-1) defined by functional tumor suppressor activity (9). Hyal-2 is anchored to the plasma membrane by a glycosylphosphatidylinositol (GPI) link. It cleaves high molecular weight HA to approximately 20 kDa fragments. It seems to function as either an oncogene or a tumor suppressor gene. Over expression of Hyal-2 accelerates tumor formation of murine astrocytoma cells (10), but can also accelerate apoptosis (11). The secretion of hyaluronidase by cancer cells can contribute to their aggressiveness and invasiveness. Thus, hyaluronidase provides the intermediate HA fragments that induce angiogenesis (12). Moreover, secretion of hyaluronidase by the cancer cell enables digestion of the HA barrier and thus facilitate invasion of tumor cells to neighboring organs and tissues. It was reported that hyaluronidase activity in ovarian cancer tissue is significantly higher than in endometrial cancer tissue. A significant correlation was found, between hyaluronidase activity and metastasis of ovarian cancer (13). Moreover, treatment of conditioned media with hyaluronidase increased the adhesion of ovarian cancer tumor cells to mesothelial monolayer which served as a model for metastatic dissemination in the peritoneal cavity (14). Since HA hyaluronidase and CD44 are involved in ovarian carcinoma (15-18), and the presence of hyaluronidase can be a sign for the presence of metastases, it is important to detect hyaluronidase activity in a non-invasive, sensitive and specific way.

To date several methods are being used for the detection of hyaluronidase including quantitative spectroscopic ELISA-like assay using avidin biotin peroxidase complex (19), a microtiter-based assay for hyaluronidase activity (20), the Morgan-Elson reaction (21) and its fluorimetric version (22) and chromatography (23). However, none of these methods can be applied in-situ for non-invasive imaging.

While reducing the present invention to practice, the present inventors designed a novel approach for in-situ detection of hyaluronidase activity, which may be used for diagnosing cancer such as, ovarian cancer.

SUMMARY OF THE INVENTION

According to one aspect of the present invention there is provided a composition-of-matter comprising a chelator moiety-hyaluronan complex bound to a solid support.

According to one aspect of the present invention there is provided use of a composition including a chelator moiety-hyaluronan complex for imaging activity of hyaluronidase in situ.

According to another aspect of the present invention there is provided a diagnostic kit comprising a chelator moiety-hyaluronan complex bound to a solid support.

According to yet another aspect of the present invention there is provided a method of assesing enzymatic activity of hyaluronidase in a biological sample, the method comprising: (a) contacting the biological sample with an indicator designed for quantifying enzymatic activity of hyaluronidase; and (b) imaging a level of the indicator in the biological sample, thereby assesing the enzymatic activity of hyaluronidase in the biological sample.

emission tomography (PET).

According to still another aspect of the present invention there is provided a method of diagnosing cancer in a subject, the method comprising: (a) administering to a subject in need thereof a indicator designed for quantifying enzymatic activity of hyaluronidase; and (b) imaging a level of the indicator in a predetermined tissue location of the subject, wherein a decrease in the level of the indicator compared to a level of the indicator in an identical predetermined tissue location of a healthy subject is indicative of cancer in the subject, thereby diagnosing the cancer in the subject.

According to still further features in the described preferred embodiments the indicator includes a chelator moiety-hyaluronan complex.

According to still further features in the described preferred embodiments the chelator moiety-hyaluronan complex is cleavable by hyaluronidase.

According to still further features in the described preferred embodiments the chelator moiety-hyaluronan complex is bound to a solid support.

According to still further features in the described preferred embodiments the solid support is a bead.

According to still further features in the described preferred embodiments the bead is an avidin-covered bead.

According to still further features in the described preferred embodiments the chelator moiety-hyaluronan complex is bound to the avidin-covered bead via a biotin linker.

According to still further features in the described preferred embodiments the biotin linker is biotinamidopentylamine.

According to still further features in the described preferred embodiments the chelator moiety is selected from the group consisting of 1,4,7,10-tetraazacyclodo-decane-N,N', N'',N'''-tetraacetic acid; 1,4,7,10-tetraaza-cyclododecane-N, N',N''-triacetic acid; 1,4,7-tris(carboxymethyl)-10-(2'-hydroxypropyl)-1,4,7,10-tetraazocyclodecane; 1,4,7-triazacyclonane-N,N',N''-triacetic acid; 1,4,8,11-tetraazacyclotetra-decane-N,N',N'',N'''-tetraacetic acid; diethylenetriamine-pentaacetic acid (DTPA); ethylenedicysteine; bis(aminoethanethiol)carboxylic acid; triethylenetetraamine-hexaacetic acid; ethylenediamine-tetraacetic acid (EDTA); 1,2-diaminocyclohexane-N,N,N',N'-tetraacetic acid; N-(hydroxy-ethyl)ethylenediaminetriacetic acid; nitrilotriacetic acid; and ethylene-bis(oxyethylene-nitrilo) tetraacetic acid.

According to still further features in the described preferred embodiments the chelator moiety is diethylenetriamine-pentaacetic acid (DTPA).

According to still further features in the described preferred embodiments the indicator further includes a metal ion or atom being attached to the chelator moiety.

According to still further features in the described preferred embodiments the metal ion or atom is a paramagnetic metal ion or atom.

According to still further features in the described preferred embodiments the metal ion or atom is a supermagnetic metal ion or atom.

According to still further features in the described preferred embodiments the metal ion or atom is a transition metal ion or atom.

According to still further features in the described preferred embodiments the metal ion or atom is a lanthanide ion or atom.

According to still further features in the described preferred embodiments the metal ion or atom is selected from the group consisting of Fe, Ni, Eu, Ho, Dy, Mn, Gd, Cr, Hf, La, Yb, Tc and In.

According to still further features in the described preferred embodiments the metal ion or atom is Gd.

According to still further features in the described preferred embodiments the imaging is effected by MRI, X-ray, light imaging, nuclear imaging and positron emission tomography (PET).

The present invention successfully addresses the shortcomings of the presently known configurations by providing compositions and methods of detecting hyaluronidase activity in situ.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In case of conflict, the patent specification, including definitions, will control. In addition, the materials, methods, and examples are illustrative only and not intended to be limiting.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

FIGS. 2a-b are representative color-coded maps of $R_2$ relaxation rate for a suspension of 1 mg/ml HA-GdDTPA-beads. FIG. 2a—Control beads suspended in water. FIG. 2b—Beads suspended in the presence of hyaluronidase. $R_2$ was measured after incubation with the contrast material for 15-30 min in 37° C.

FIGS. 3a-c are photomicrographs depicting the expression of hyaluronidase in ovarian carcinoma cells. FIGS. 3a-b—show the expression of HYAL1 and HYAL2, respectively, as determined by semi-quantitative RT-PCR. mRNA levels of the two genes were measured in ES-2 and OVCAR-3 human carcinoma cell lines. S16 served as an internal control. FIG. 3c—show protein expression levels of Hyal-1 and Hyal-2 in OVCAR-3 and ES-2 cells, as determined by Western blot analysis.

FIGS. 4a-e depict the secretion of biologically active hyaluronidase by ovarian carcinoma cells, as determined by particle exclusion assay, measuring the hyaluronan coat of chondrocytes by exclusion of fixed red blood cells. FIG. 4a—Chondrocytes incubated in fresh medium. FIG. 4b-Chondrocytes incubated with fresh medium in the presence of bovine testes hyaluronidase (300 µg/ml for 15-30 min). FIGS. 4c-d—Chondrocytes incubated with medium conditioned by OVCAR-3 or ES-2, respectively. FIG. 4e-Analysis of the relative change in area of the hyaluronan coat for FIGS. 4a-d. Activity of hyaluronidase is manifested by reduced area.

FIGS. 5a-b depict Hyaluronidase secretion by ovarian carcinoma cells as determined by HA-GdDTPA-beads in MRI imaging. FIG. 5a is a representative color-coded map of R2 relaxation which was derived for HA-GdDTPA-beads suspended in fresh medium (left), or in conditioned medium collected from OVCAR-3 (center) or ES-2 (right) human epithelial ovarian carcinoma cells. FIG. 5b-ES-2 and OVCAR-3 human epithelial ovarian carcinoma cells were grown in 96 well plate. HA-GdDTPA-beads were added for 15-30 min. The R2 relaxation rate of the medium was measured by MRI (using a slice above the cell layer).

DESCRIPTION OF THE PREFERRED EMBODIMENTS

Figure 1:
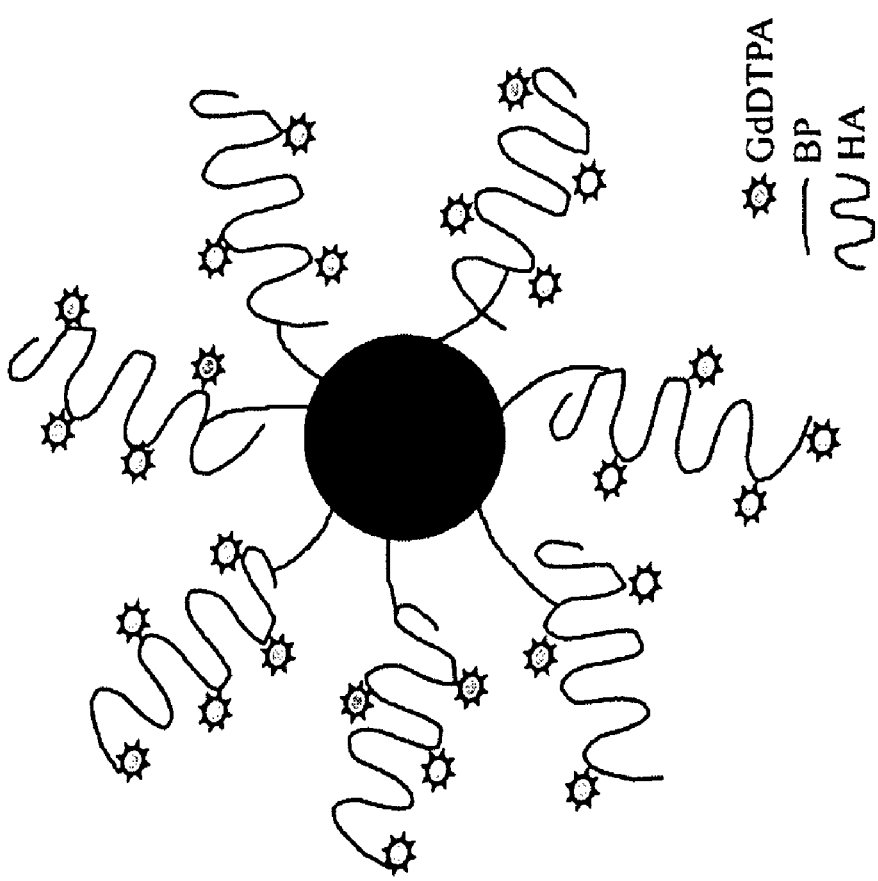
FIG. 1 is scheme depicting HA-GdDTPA. GdDTPA was covalently linked to hyaluronan, and the complex was attached to agarose-avidin beads via BP (Biotinamidopentylamine). In general, degradation of the hyaluronan contrast agent of the present invention by hyaluronidase to low molecular weight fragments alters R2 relaxivity and thus changes signal intensity in T2 weighted images.

The present invention is of compositions for detecting hyaluronidase activity in situ. Specifically, the present invention can be used for in-situ diagnosis of cancer, such as ovarian cancer.

The principles and operation of the present invention may be better understood with reference to the drawings and accompanying descriptions.

Before explaining at least one embodiment of the invention in detail, it is to be understood that the invention is not limited in its application to the details set forth in the following description or exemplified by the Examples. The invention is capable of other embodiments or of being practiced or carried out in various ways. Also, it is to be understood that the phraseology and terminology employed herein is for the purpose of description and should not be regarded as limiting.

Hyaluronan, a high molecular weight, negatively charged polysaccharide is a major constituent of the extracellular matrix. Previous studies demonstrated a role of hyaluronan in adhesion of cancer cells, including ovarian carcinoma, through interaction with the cell surface receptor CD44. High molecular weight hyaluronan is antiangiogenic, however its degradation by hyaluronidase generates proangiogenic breakdown products. Thus, by expressing hyaluronidase, cancer cells can tilt the angiogenic balance of their microenvironment and allow invasion thereof. Hence, hyaluronidase activity can serve as a reliable diagnostic tool for cancer and metastasis.

Currently available methods for detecting hyaluronidase activity or levels, include quantitative spectroscopic ELISA-like assay using avidin biotin peroxidase complex (19), a microtiter-based assay for hyaluronidase activity (20), the Morgan-Elson reaction (21) and its fluorimetric version (22) and chromatography (23). However, none of these methods can be applied for non-invasive in-situ imaging.

While reducing the present invention to practice, the present inventors designed a novel approach for assessing hyaluronidase activity in-situ. This method can be used for single-step detection of cancer, such as ovarian cancer.

As is illustrated hereinbelow and in the Examples section which follows, the present inventors designed a novel hyaluronidase indicator generated by linking Gd-DTPA hyaluronan to the surface of agarose beads. These non-toxic beads showed pronounced alternations in $R_2$ relaxation rate induced by hyaluronidase. Thus, the hyaluronidase indicator of the present invention can be used for the detection of hyaluronidase in tumors such as ovarian carcinoma, in which hyaluronidase is associated with metastatic spread to the peritoneum.

In sharp contrast to previously described methods of in situ imaging of hyaluronan for the detection of cancer (U.S. Pat. No. 5,772,982), the present invention is not aimed at assessing the localization of hyaluronan in situ, but rather at assessing breakdown thereof by hyaluronidase, thereby assessing the amount of biologically active hyaluronidase which is important for cancer progression to thereby provide a far more sensitive diagnostic assay.

Thus, according to one aspect of the present invention there is provided a method of assessing enzymatic activity of hyaluronidase in a biological sample.

As used herein the phrase "enzymatic activity of hyaluronidase" refers to the catalytic activity of mammalian hyaluronidase (e.g., hyaluronoglucosamimidase activity) or any biological activity associated therewith (e.g., invasion). Preferably mammalian hyaluronidase refers to human hyaluronidase [e.g., hyal-1 (GenBank Accession No. NM_007312), hyal-2, PH-20, MGEA5 and hyal-3].

As used herein the phrase "biological sample" refers to a sample of tissue or fluid isolated from an individual, including, but not limited to, for example, plasma, serum, spinal fluid, lymph fluid, the external sections of the skin, respiratory, intestinal, and genitourinary tracts, tears, saliva, milk, blood cells, synovial cell fluid, cells, tumors, organs such as synovial tissue and also samples of in vivo cell culture constituents (e.g., synovial fluid cells).

The method according to this aspect of the present invention is effected by contacting the biological sample with an indicator designed for quantifying enzymatic activity of hyaluronidase; and imaging a level of the indicator in the biological sample, thereby assesing the enzymatic activity of hyaluronidase in the biological sample.

As used herein the term "indicator" refers to a substance, which produces a detectable signal in response to the presence of a particular material in a sample. As mentioned, the indicator of the present invention is selected to quantify the enzymatic activity of hyaluronidase.

A specific example of such an indicator is described hereinbelow and in the Examples section, which follows.

As mentioned, the level of the indicator in the biological sample is detected by imaging.

As used herein the term "imaging" refers to the process of producing images of internal organs of the body or of the biological sample. Examples of imaging procedures which can be used in accordance with the method of the present invention include, but are not limited to, MRI, X-ray, light [visible and near infrared (NIR)] imaging, nuclear imaging and positron emission tomography (PET). According to presently known embodiments of the present invention, the imaging procedure is MRI.

The indicator (i.e., signal generating moiety thereof) is designed and configured based on the imaging procedure used. For example for light imaging a fluorescent moiety is preferably used. Thus, when chemically linked to hyaluronan, contacted with the sample and exposed to light of an appropriate wavelength, a reduced fluorescent level will appear in the region of the tumor due to degradation thereof by hyaluronidase. This is particularly useful in detecting and diagnosing skin cancers and oral cancers. Examples of fluorescent dyes which can be used to label hyaluronan include fluorescein, which appears bright green when exposed to ultraviolet (UV) light; auramine 0, which appears yellow when exposed to UV light; and hematoporphyrin and rhodamine. B, which appear red upon exposure to UV light. Tumors inside the body can be exposed to light and visualized with this method by utilizing a fiberoptic scope. Image intensifiers and wavelength detectors may be necessary to intensify the image, particularly for small tumors.

As mentioned hereinabove, the present inventors designed compounds which can be used as hyaluronidase indicators.

Thus, according to another aspect of the present invention there is provided a composition including chelator moiety-hyaluronan complex, which is preferably bound to a solid support.

The chelator moiety-hyaluronan complex is preferably cleavable by hyaluronidase and as such can be used in diagnostic applications.

As used herein the phrase "solid support" refers to a biocompatible substance (i.e., a substance which upon administration to a subject, does not elicit a detrimental response sufficient to result in the rejection of the support or to render it inactive, for example through degradation) capable of binding the chelator moiety-hyaluronan complex and elevating a local concentration thereof in a particular body tissue or site following administration (i.e., bio-distribution modifier see e.g., U.S. Pat. No. 5,801,228 and references therein). The solid support of the present invention is preferably insoluble. Examples of substances which can be used to generate the solid support of the present invention include, but are not limited to, glass, polystyrene, polypropylene, polyethylene, dextran, nylon, amylases, natural and modified celluloses, polyacrylamides, agaroses, and magnetite. A preferred configuration of the solid support of the present invention is spherical such as a bead. Other configurations of the solid support of the present invention, include but are not limited to, flat configurations such as a sheet.

Suitable methods for immobilizing (i.e., binding) the chelator moiety-hyaluronan complex to the solid support are known in the art and may involve ionic, hydrophobic, van der Waals or covalent interactions. Immobilization of the chelator moiety-hyaluronan complex to the solid support may be mediated via a linker (e.g., biotinamidopentylamine, see Example 1 of the Examples section.

As used herein "a chelator moiety" refers to a synthetic or natural material which is capable of stably binding (i.e., chelating) a metal ion or atom. The chelator moiety can be synthetic or natural organic compounds known to bind metal ions or atoms, or any molecule of biological origin, or by-product or modified product of a molecule of biological origin, such as proteins, sugars or carbohydrates, lipids and nucleic acids, and any combination thereof, that may bind ions or atoms. Examples of chelator moieties which can be used in accordance with the present invention include, but are not limited to, 1,4,7,10-tetraazacyclodo-decane-N,N',N'',N'''-tetraacetic acid; 1,4,7,10-tetraaza-cyclododecane-N,N',N''-triacetic acid; 1,4,7-tris(carboxymethyl)-10-(2'-hydroxypropyl)-1,4,7,10-tetraazocyclodecane; 1,4,7-triazacyclonane-N,N',N''-triacetic acid; 1,4,8,11-tetraazacyclotetra-decane-N,N',N'',N'''-tetraacetic acid; diethylenetriamine-pentaacetic acid (DTPA); ethylenedicysteine; bis(aminoethanethiol)carboxylic acid; triethylenetetraamine-hexaacetic acid; ethylenediamine-tetraacetic acid (EDTA); 1,2-diaminocyclohexane-N,N,N',N'-tetraacetic acid; N-(hydroxy-ethyl)ethylenediaminetriacetic acid; nitrilotriacetic acid; and ethylene-bis(oxyethylene-nitrilo) tetraacetic acid.

According to presently known embodiments of this aspect of the present invention the chelator moiety is diethylenetriamine-pentaacetic acid (DTPA).

The composition of the present invention may further include a metal ion or atom being attached to the chelator moiety. The identity of the metal ion or atom largely depends on the intended use of the composition of the present invention.

For example, for use in MRI applications, the compositions of the present invention may be metallated by supermagentic metal ions or atoms, paramagnetic metal ions or atoms or polyatomic cluster ions or atoms (e.g. polyoxoanion and their sulphur analogues), for example transition metal or lanthanide metal ions or atoms. Examples of such metal ions or atoms include, but are not limited to transition metals or lanthanides, preferably having an atomic number of 21 to 29, 42, 44 or 57 to 71. Fe, Ni, Eu, Ho, Dy, Mn, Gd, Cr, Hf, La, Yb, Tc and In are especially preferred.

It will be appreciated that for use as contrast agents in MRI, the metal species is preferably non-radioactive, as radioactivity is a characteristic which is neither required nor desirable for MR diagnostic contrast agents.

The compositions of the invention may however also be used to carry other metal ions or atoms for use in different diagnostic imaging modalities.

For example, for use as X-ray or ultrasound contrast agents, the metal species is preferably a heavy metal species, for example a non-radioactive metal with an atomic number greater than 37, preferably greater than 50, such as for example $Dy^{3+}$.

Alternatively, for use in radionuclide imaging, the metal species is radioactive. Examples of radioactive ions or atoms include, but are not limited to $^{99}Tc$, $^{67}Ga$ or $^{111}In$.

As mentioned hereinabove, the compositions of the present invention include Hyaluronan which is cleaved by hyaluronidase.

As used herein "hyaluronan" refers to a high molecular glycosaminoglycan (~700 kDa), composed of repeating disaccharides of glucuronic acid and N-acetylglucosamine. Hyaluronan may be purified as described by Mohoney (2001) Glycobiology 11:1025-1033 or purchased from commercial vendors such as Sigma Chemical Co., St. Louis, Mo. (Cat. No. B1557).

The indicator molecules of the present invention can be synthesized using well known chemical synthesis procedures. Attachment of hyaluronan to the chelator moiety is described in details in the "Materials and Experimental Procedures" section of the Examples section which follows.

The present inventors have successfully exhibited differences in hyaluronidase activity in different ovarian carcinoma cell lines (see Example 5 of the Examples section) using the above-described methodology, suggesting the use of the above described imaging procedure for the diagnosis of cancer.

Thus according to yet another aspect of the present invention there is provided a method of diagnosing cancer in a subject.

As used herein the term "diagnosing" refers to classifying a disease or a symptom as cancer, typing the cancer, determining a severity of the cancer (e.g., staging, localizing), monitoring disease progression, forecasting an outcome of a disease and/or prospects of recovery.

As used herein the term "cancer" refers to a disease characterized by uncontrolled growth of cells wherein the resultant tumor is featured by enhanced hyaluronidase activity. Examples of cancer which can be diagnosed according to this aspect of the present invention include, but are not limited to, colonic adenocarcinomas, lung cancers (e.g., squamous cell carcinoma, small- and large-cell undifferentiated carcinomas and adenocarcinomas), kidney cancers, uterine and cervical cancers, prostate cancer, bladder cancer, ovarian cancer, esophageal cancers, liver cancers (e.g., hepatocarcinomas), pancreatic cancer, stomach cancer, liposarcoma, synovial sarcoma, rhabdomyosarcoma, chondrosarcoma, osteosarcoma, Ewing's tumor, testicular and ovarian dysgerminoma, retinoblastoma, Wilms' tumor, neuroblastoma, malignant melanoma, mesothelioma, Gardner's syndrome, basal cell carcinoma, breast cancers (including adenocarcinomas and medullary carcinomas), lymphoma, medulloblastoma, choriocarcinoma, Paget's disease, multiple myeloma, glioblastoma, Burkitt's lymphoma and Kaposi's sarcoma (see U.S. Pat. No. 5,772,982). According to presently known embodiments of this aspect of the present invention the method is preferably directed at diagnosing ovarian cancer.

As used herein the term "subject" refers to a mammal, preferably a human subject who has cancer or is predisposed to developing cancer.

The method according to this aspect of the present invention is effected by administering to a subject in need thereof, the above described indicator; and imaging a level of the indicator in a predetermined tissue location of the subject, wherein a decrease in the level of the indicator compared to a level of the indicator in an identical predetermined tissue location of a healthy subject is indicative of cancer in the subject, thereby diagnosing the cancer in the subject.

It will be appreciated that a healthy subject, according to this aspect of the present invention, does not have at least the disease of interest (e.g., ovarian cancer). However, it will be appreciated that images (such as those stored in databases) of healthy tissues may also be used.

Indicator molecules of the present invention can be provided to the subject per se, or as part of a pharmaceutical composition where they are mixed with a pharmaceutically acceptable carrier.

As used herein a "pharmaceutical composition" refers to a preparation of one or more of the active ingredients described herein (i.e., agents) with other chemical components such as physiologically suitable carriers and excipients. The purpose of a pharmaceutical composition is to facilitate administration of a compound to an organism.

Herein the term "active ingredient" refers to the indicator molecule.

Hereinafter, the phrases "physiologically acceptable carrier" and "pharmaceutically acceptable carrier" which may be interchangeably used refer to a carrier or a diluent that does not cause significant irritation to an organism and does not abrogate the properties of the administered compound. An adjuvant is included under these phrases. One of the ingredients included in the pharmaceutically acceptable carrier can be for example polyethylene glycol (PEG), a biocompatible polymer with a wide range of solubility in both organic and aqueous media (Mutter et al. (1979).

Herein the term "excipient" refers to an inert substance added to a pharmaceutical composition to further facilitate administration of an active ingredient. Examples, without limitation, of excipients include calcium carbonate, calcium phosphate, various sugars and types of starch, cellulose derivatives, gelatin, vegetable oils and polyethylene glycols.

Techniques for formulation and administration of drugs may be found in "Remington's Pharmaceutical Sciences," Mack Publishing Co., Easton, Pa., latest edition, which is incorporated herein by reference.

Suitable routes of administration may, for example, include oral, rectal, transmucosal, especially transnasal, intestinal or parenteral delivery, including intramuscular, subcutaneous and intramedullary injections as well as intrathecal, direct intraventricular, intravenous, intraperitoneal, intranasal, or intraocular injections.

For MRI and X-ray imaging, the most preferred mode for administering the indicator molecules of the present invention is parenteral, for example intravenous, administration. However, other administration routes can be used dependent on the localization of the tumor. For example, for ovarian cancer which invades the peritoneum a preferred administration route is intraperitoneal.

When the indicator includes a heavy metal ion, it may be desirable to include within the formulation a slight excess of the chelating agent, for example as discussed by Schering in DE-A-3640708, or more preferably a slight excess of the calcium salt of such a chelating agent.

Pharmaceutical compositions of the present invention may be manufactured by processes well known in the art, e.g., by means of conventional mixing, dissolving, granulating, dragee-making, levigating, emulsifying, encapsulating, entrapping or lyophilizing processes.

Pharmaceutical compositions for use in accordance with the present invention may be formulated in conventional manner using one or more physiologically acceptable carriers comprising excipients and auxiliaries, which facilitate processing of the active ingredients into preparations which, can be used pharmaceutically. Proper formulation is dependent upon the route of administration chosen.

For injection, the active ingredients of the invention may be formulated in aqueous solutions, preferably in physiologically compatible buffers such as Hank's solution, Ringer's solution, or physiological salt buffer. For transmucosal administration, penetrants appropriate to the barrier to be permeated are used in the formulation. Such penetrants are generally known in the art.

For oral administration, the compounds can be formulated readily by combining the active compounds with pharmaceutically acceptable carriers well known in the art. Such carriers enable the compounds of the invention to be formulated as tablets, pills, dragees, capsules, liquids, gels, syrups, slurries, suspensions, and the like, for oral ingestion by a patient. Pharmacological preparations for oral use can be made using a solid excipient, optionally grinding the resulting mixture, and processing the mixture of granules, after adding suitable auxiliaries if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carbomethylcellulose; and/or physiologically acceptable polymers such as polyvinylpyrrolidone (PVP). If desired, disintegrating agents may be added, such as cross-linked polyvinyl pyrrolidone, agar, or alginic acid or a salt thereof such as sodium alginate.

Dragee cores are provided with suitable coatings. For this purpose, concentrated sugar solutions may be used which may optionally contain gum arabic, talc, polyvinyl pyrrolidone, carbopol gel, polyethylene glycol, titanium dioxide, lacquer solutions and suitable organic solvents or solvent mixtures. Dyestuffs or pigments may be added to the tablets or dragee coatings for identification or to characterize different combinations of active compound doses.

Pharmaceutical compositions, which can be used orally, include push-fit capsules made of gelatin as well as soft, sealed capsules made of gelatin and a plasticizer, such as glycerol or sorbitol. The push-fit capsules may contain the active ingredients in admixture with filler such as lactose, binders such as starches, lubricants such as talc or magnesium stearate and, optionally, stabilizers. In soft capsules, the active ingredients may be dissolved or suspended in suitable liquids, such as fatty oils, liquid paraffin, or liquid polyethylene glycols. In addition, stabilizers may be added. All formulations for oral administration should be in dosages suitable for the chosen route of administration.

For buccal administration, the compositions may take the form of tablets or lozenges formulated in conventional manner.

For administration by nasal inhalation, the active ingredients for use according to the present invention are conveniently delivered in the form of an aerosol spray presentation from a pressurized pack or a nebulizer with the use of a suitable propellant, e.g., dichlorodifluoromethane, trichlorofluoromethane, dichloro-tetrafluoroethane or carbon dioxide. In the case of a pressurized aerosol, the dosage unit may be determined by providing a valve to deliver a metered amount. Capsules and cartridges of, e.g., gelatin for use in a dispenser may be formulated containing a powder mix of the compound and a suitable powder base such as lactose or starch.

The preparations described herein may be formulated for parenteral administration, e.g., by bolus injection or continuous infusion. Formulations for injection may be presented in unit dosage form, e.g., in ampoules or in multidose containers with optionally, an added preservative. The compositions may be suspensions, solutions or emulsions in oily or aqueous vehicles, and may contain formulatory agents such as suspending, stabilizing and/or dispersing agents.

Pharmaceutical compositions for parenteral administration include aqueous solutions of the active preparation in water-soluble form. Additionally, suspensions of the active ingredients may be prepared as appropriate oily or water based injection suspensions. Suitable lipophilic solvents or vehicles include fatty oils such as sesame oil, or synthetic fatty acids esters such as ethyl oleate, triglycerides or liposomes. Aqueous injection suspensions may contain substances, which increase the viscosity of the suspension, such as sodium carboxymethyl cellulose, sorbitol or dextran. Optionally, the suspension may also contain suitable stabilizers or agents which increase the solubility of the active ingredients to allow for the preparation of highly concentrated solutions.

Alternatively, the active ingredient may be in powder form for constitution with a suitable vehicle, e.g., sterile, pyrogen-free water based solution, before use.

The preparation of the present invention may also be formulated in rectal compositions such as suppositories or retention enemas, using, e.g., conventional suppository bases such as cocoa butter or other glycerides.

Pharmaceutical compositions suitable for use in context of the present invention include compositions wherein the active ingredients are contained in an amount effective to achieve the intended purpose.

Toxicity and diagnostic efficacy of the active ingredients described herein can be determined by standard pharmaceutical procedures in vitro, in cell cultures or experimental animals. The data obtained from these in vitro and cell culture assays and animal studies can be used in formulating a range of dosage for use in human. The dosage may vary depending upon the dosage form employed and the route of administration utilized. The exact formulation, route of administration and dosage can be chosen by the individual physician in view of the patient's condition. [See e.g., Fingl, et al., (1975) "The Pharmacological Basis of Therapeutics", Ch. 1 p.1].

For MR diagnostic examination, the diagnostic agent of the present invention, if in solution, suspension or dispersion form, will generally contain the indicator at a concentration in the range 0.1-10 mg/ml. The indicator however may be supplied in a more concentrated form for dilution prior to administration. For example, a Gd-indicator of the present invention is preferably administered so as to reach a Gd concentration of 0.1-1 mM at the site of hyaluronidase activity.

For X-ray examination, the dose of the contrast agent should generally be higher and for scintographic examination the dose should generally be lower than for MR examination.

It will be appreciated that the indicator molecules of the present invention can be included in a diagnostic or therapeutic kit. For example, indicator sets including one or more of the following components described hereinabove (i.e., an indicator molecule, a mobilizing agent, manganate, a non-labeled iron chelator, an apo-transferrin binding metal other than iron, an anti-apo transferrin antibody, anionic beads), can be packaged in a one or more containers with appropriate buffers and preservatives and used for diagnosis or for directing therapeutic treatment.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Reference is now made to the following examples, which together with the above descriptions, illustrate the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683, 202; 4,801,531; 5,192,659 and 5,272,057; "Cell Biology: A Laboratory Handbook", Volumes I-III Cellis, J. E., ed. (1994); "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "nucleic Acid Hybridization" Hames, B. D., and Higgins S. J., eds. (1985); "Transcription and Translation" Hames, B. D., and Higgins S. J., Eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

Materials and Experimental Procedures

Synthesis of HA-GdDTPA-beads—HA-GdDTPA was synthesized as described (24). Briefly; Hyaluronan (HA; 50 mg, from human umbilical cord; Sigma Chemical Co., St. Louis, Mo.) was dissolved in 2-(N-Morpholino) ethanesulfonic acid (MES; pH 4.75, 0.1M; Sigma) to a final concentration of 1 mg/ml. The carboxyl groups of HA were activated by addition of 2.4 mg N-(3-Dimethylaminopropyl)-N-ethylcarbodiimide hydrochloride (EDC) followed by addition of 2 mg Ethylenediamine (EDA). The reaction mixture was stirred over night at room temperature and the product was purified by dialysis against DDW. The clean product was reacted in DDW with 18.7 mg diethylene triamine pentaacetic acid anhydride (DTPA; Sigma) dissolved in 55 ml of Dimethyl sulfoxide (DMSO) over night at room temperature and was dialyzed again against DDW. Gadolinium (III) chloride ($GdCl_3$; 23.5 mg, Sigma) in DDW was added, the mixture was stirred for 24 hours and a third dialysis was performed.

HA-GdDTPA was further covalently bound to avidin agarose beads (0.040-0.165 mm). Avidin linked agarose beads (0.05 ml of beads that contain $6e^{-9}$ mol avidin, Sigma) were mixed with 2 μg 5-(Biotinamido)pentylamine (BP; Pierce) in MES buffer (pH 5.5, 0.1M) at room temperature in order to let the biotin in the BP link to the avidin on the agarose beads. The Carboxyl groups of HA-GdDTPA (25 mg HA-GdDTPA) were activated in MES buffer by 2 mg EDC, and added to BP pre-conjugated beads. The reaction was stirred at room temperature over night and the product was purified by dialysis against DDW. In contrast with the source agarose beads, HA-GdDTPA-beads are hydrated and generate a clear and stable suspension (the beads alone are non transparent and tend to settle rapidly).

Cell culture—Human ovarian carcinoma cell lines, ES-2 and OVCAR-3, were kindly given by Prof. Steffen Hauptmann, Institute of pathology, "Rudolf-Virchow-Haus", Berlin. ES-2 and OVCAR-3 cells were cultured in Dulbecco's minimum essential medium (DMEM) supplemented with 10% fetal calf serum (FCS). Chondrocytes (RCJ-P, Rat chondrocytes from fetal calvaria, batch 15.01.98; Prochon Biotec Ltd. Israel) were cultured in α-minimum essential medium (αMEM) supplemented with 15% FCS. All media were supplemented with 100 u/ml penicillin, 0.1 mg/ml streptomycin and 0.06 mg/ml amphotericin and 0.292 mg/ml L-glutamine.

MRI studies—The enzyme that was used was either a commercially purified hyaluronidase (Sigma, Type IV-S from bovine testes, 0.3 mg/ml) or hyaluronidase found in a conditioned medium of ovarian carcinoma cell lines.

MRI microscopy measurements were performed on a 400 MHz (9.4 Tesla) wide-bore DMX bruker spectrometer, equipped with a microimaging attachment with a 5 mm Helmholtz radio frequency (RF) coil or horizontal 4.7T Biospec (Bruker, Karlsruhe, Germany). A series of spin echo images, with TR 2000 ms and 8 different TE ranging between 10 and 80 ms (2 averages, FOV 1×1 cm, slice thickness 1 mm, matrix 128×128, SW=50,000 Hz) were acquired.

Analysis of MR data—MRI data was analyzed on a personal computer using Matlab (The Math Works Inc. Natick, Mass.). Images acquired with 8 different TE values were used for generation of $R_2$ maps by non-linear least square pixel-by-pixel fitting to a single exponent (Eq. 1)

$$I = A\, e^{-TE*R2} \quad [1]$$

Where I is the measured signal intensity for each TE, A is the fitted steady state signal intensity in fully relaxed images. $R_2$ values were averaged and standard deviation was calculated.

Particle exclusion assay—Chondrocytes were grown to confluence in a 10 cm culture dish, diluted 1:100 and seeded on a particle exclusion assay plate (35 mm Petri dish with 14 mm microwell; MatTek, Ashland, Mass.). After over night incubation, the medium was replaced by DMEM, hyaluronidase in PBS, or by conditioned medium removed from different ovarian carcinoma cell lines. After 1 h in 37° C., the medium was replaced by human red blood cells type O (sigma) diluted in DMEM. Samples were viewed in visible light using Axioskop microscope (Zeiss, Oberkochen, Germany). Images were acquired using a scientific-grade cooled charged-coupled device (CCD) camera (Model CC350 Photometrics Co., AZ). The experiment was repeated five times, in each at least five cells from a particular treatment were measured.

Reverse Transcription PCR—Total RNA was extracted using TRI-REAGENT ™ (Molecular Research Center, Inc. Cincinnati, Ohio) according to the manufacturer instructions and reverse transcribed in 0.02 ml volumes using RNase reverse transcriptase (Super-Script™ II, Invitrogen Life Technologies, Inc. Carlsbad, Calif.) with 180 pmol hexamer random primer. Aliquots (0.002 ml) of reverse transcription products were used for PCR. The following sense and anti-sense primers were used: for Hyal2 (GenBank Accession No: U09577), sense: gctcaagcccacagcaccac (SEQ ID NO: 1) and anti-sense: cagtgtctccagcatgaactgc (SEQ ID NO: 2), Hyal1 (GenBank Accession No: U96078, 25) sense: caccgtctggaatgcaaaca (SEQ ID NO: 3), anti-sense: gttggctaccacatcgaagaca (SEQ ID NO: 4). PCR parameters for Hyal1: 3 min 94° C., 31 cycles of 20 s 94° C., 30 s 58° C., 45 s 72° C., followed by 3 min 72° C. For Hyal2: 3 min 94° C., 24 cycles of 20 s 94° C., 30 s 60° C., 45 s 72° C., followed by 3 min 72° C. S16 was used for internal control.

Western blotting analysis—Confluent ovarian carcinoma cells OVACR-3 and ES-2 were washed with serum-free DMEM and were incubated in this medium for 24 or 48 h. The medium was collected, centrifuged in order to remove cells, and was concentrated using Amicon Ultra 10,000 MWCO (Millipore, Bedford, Mass.). Equal amounts of protein (0.04 mg/lane for Hyal-1 and 0.06 mg/lane for Hyal-2; Bradford method) were electrophoresed (12% SDS-polyacrylamide gel). Blocked membranes (5% milk in TBST; 1 h, RT) were incubated overnight at 4° C. with either anti-Hyal-1 or anti-Hyal-2 polyclonal antibody. Membranes were washed (×3) with TBST and incubated with horseradish peroxidase labeled antibodies (1:10,000; ZYMED Inc., San Francisco, Calif.). The immunoreactive bands were detected by ECL. The intensity of the signal was quantitated by computerized densitometry (Quantity One, BioRad).

Example 1

Detection of Hyaluronidase Activity by MRI using HA-GdDTPA-Beads

Avidin-agarose beads, were covalently linked via the avidin moiety to HA-GdDTPA (FIG. 1), in order to develop a contrast material for non-invasive imaging of hyaluronidase activity by MRI. Suspension of HA-GdDTPA-beads (1 mg/ml) was used to test the ability of MRI to detect hyal-dependent changes in the $R_2$ relaxation rate of water.

As shown in FIGS. 2a-b, a significant increase in $R_2$ was measured for beads supplemented with the commercial hyaluronidase relative to control HA-GdDTPA-beads suspended in pure DDW (1 tail t-test unpaired p=0.0047).

Example 2

Expression of Hyal-1 and Hyal-2 in Ovarian Carcinoma Cells

The expression of hyaluronidase 1 and 2 was measured in two human epithelial ovarian carcinoma cell lines: OVCAR-3 and ES-2. Semi-quantitative Reverse Transcription PCR showed no significant difference in the mRNA levels of HYAL-1 or HYAL-2 between those 2 cell lines (FIGS. 3a-b).

In contrast with the similarity in mRNA expression, the amount of hyaluronidase released to the culture medium was significantly different. The conditioned medium of the cells was analyzed by Western blot analysis using anti-Hyal-1 and anti-Hyal-2 antibodies. A large difference was detected in the amount of hyaluronidase secreted by OVCAR-3 and ES-2 cells (FIG. 3c). Medium conditioned by ES-2 cells demonstrated high levels of both Hyal-1 and Hyal-2, while in medium conditioned by OVCAR-3 cells the proteins were un-detectable. Although ES-2 cells exhibit higher rate of proliferation in 10% FCS, they showed decreased cell survival in serum free medium relative to OVCAR-3 cells. Thus, conditioned medium was collected in most experiments 24 h after serum removal.

Example 3

Secretion of Active Hyaluronidase by Human Epithelial Ovarian Carcinoma Cells

Particle exclusion assay was used to evaluate the activity of hyaluronidase secreted by ovarian carcinoma cells (FIGS. 4a-e). The chondrocytes used in this assay were surrounded by a thick pericellular coat comprised of high molecular weight HA, which excludes red blood cells. Hence, red blood cells which are added to the culture plate, surround the HA layer, delineating it and thereby allowing its visualization (FIG. 4a). Upon addition of hyaluronidase, the high molecular weight HA is degraded, allowing the red blood cells to approach the chondrocyte membrane (FIG. 4b).

The activity of hyaluronidase in medium conditioned by OVCAR-3 and ES-2 ovarian carcinoma cells was examined by addition of this medium to the chondrocytes (FIG. 4c-d). Conditioned medium from ES-2 cells degraded the HA layer and showed significantly higher activity of hyaluronidase relative to conditioned medium from OVCAR-3 cells (1 tail t-test unpaired p=0.02; FIG. 4e).

Example 5

MRI Detection of Hyaluronidase Activity in Medium Conditioned By Ovarian Carcinoma Cells HA-GdDTPA-beads were added to a 96 well plate in which ES-2 and OVCAR-3 cells were grown to confluence. Non-treated medium and hyaluronidase containing medium served as negative and positive controls respectively. hyaluronidase expressed by tumor cells induced an elevation in $R_2$ (FIGS. 5a-b). ES-2 cells that showed high secretion of biologically active hyaluronidase in the exclusion assay, also showed the largest increase in $R_2$ relaxation rate, whereas the change in $R_2$ in OVCAR-3 cells well was similar to that of serum containing medium without hyaluronidase. The difference in $R_2$ between ES-2 and OVCAR-3 was significant (1 tail t-test unpaired p=0.004) as well as between ES-2 and the negative control (1 tail t-test unpaired p=0.01). There was no significant difference between OVCAR-3, fresh medium or commercial hyaluronidase containing medium.

The change in $R_2$ could be induced by hyaluronidase that was secreted to the medium and reacted with the contrast material to degrade it. Alternatively, the change could be attributed to hyaluronidase that is anchored to the cells surface (26).

In order to differentiate between the two options, conditioned medium from ES-2 or OVCAR-3 cells (depleted of residual cells by centrifugation) was tested, yielding $R_2$ values similar to those obtained in the presence of cells (FIG. 5b). HA-GdDTPA-beads suspended in conditioned medium of ES-2 cells showed larger increase in $R_2$ than that observed for OVCAR-3 cells (1 tail t-test unpaired p<0.0001). Thus, the effect detected by MRI was consistent with the level and biological activity of hyaluronidase secreted by these two ovarian carcinoma cell lines.

Discussion

Molecular imaging, aimed at detection of specific enzymatic reaction by MRI, is a novel exciting approach for non invasive characterization of processes in living organisms (27). Examples for such approaches include agents developed for MRI of beta-galactosidase (28), proteases (27, 29) and iron binding proteins such as tryrosinase (30), transferrin receptor (31, 32), and ferritin (33). A number of those exploit the change in relaxivity that occurs upon changes in the rotation time, changes in the number of water molecules in the first coordination sphere. The large number of mechanisms by which magnetic relaxivity can change offers many possibilities for design of new approaches and for targeting different enzymatic reactions. The aim of the present study was to develop contrast material for detection of Hyaluronidase, a key enzyme affecting the angiogenic balance of the extracellular matrix, by mediating breakdown of anti-angiogenic high molecular weight HA into its low molecular weight pro-angiogenic products.

A single step, in situ assay for detection of Hyaluronidase, which potentially could be adapted for non invasive in-vivo imaging by MRI is reported herein. Using beads enveloped with HA-GdDTPA it was possible to detect changes in $R_2$ relaxation rate after addition of either hyaluronidase or conditioned medium taken from ovarian carcinoma cell line that express and secrete hyaluronidase. In the presence of HA-GdDTPA-beads, $R_2$ increased significantly upon interaction with hyaluronidase. The relative contribution to the observed changes in relaxation rate, i.e. degradation of HA-GdDTPA versus binding of hyaluronidase to the contrast material, remains to be differentiated. Hypothetically, degradation of HA can cause a release of GdDTPA or low MW HA-GdDTPA to the surrounding water, which might allow increased interaction with water and effect $R_2$. Similarly, binding of hyaluronidase to HA could change the conformation of HA and expose GdDTPA to water, possibly by interfering with a direct interaction of the negatively charged carboxyl groups of hyaluronan with the free coordination sites of Gd which will also elevate $R_2$.

The ability to detect physiological levels of hyaluronidase by MRI using HA-GdDTPA-beads, was tested in vitro using human epithelial ovarian carcinoma cells. The expression of Hyal-1 and Hyal-2 were evaluated in OVCAR-3 and ES-2 human ovarian carcinoma cell lines. While no significant difference was found in the levels of mRNA for the two cell lines, Western blot analysis revealed a large difference in the protein levels of Hyal-1 and Hyal-2 secreted to the culture medium. ES-2 cells secreted high levels of both hyaluronidases to the medium, while in an equivalent amount of total protein, both Hyal-1 and Hyal-2 were undetectable in OVCAR-3 cells medium. Traces of Hyal-1 and Hyal-2 could be detected in medium from OVCAR-3 cells by using a double amount of protein (data not shown). These findings suggest that secretion of Hyal-1 and 2 might be regulated at the protein level (translation or degradation).

The biological activity of hyaluronidase, as manifested by degradation of the hyaluronan coat of chondrocytes using the particle exclusion assay, revealed that ES-2 cells not only secrete more hyaluronidase but also the activity of hyaluronidase, secreted by ES-2 cells, is higher relative to OVCAR-3 cells. Remarkably, the MRI contrast material reported here, HA-GdDTPA-beads was able to detect hyaluronidase when added to solution and also when secreted by human ovarian carcinoma cells. Moreover, the contrast material was sensitive to the different levels of hyaluronidase between the two ovarian cell lines and the changes in $R_2$ were consistent with the Western blot and particle exclusion assay, all of which showed higher levels of hyaluronidase in the ES-2 cells.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications and GenBank Accession numbers mentioned in this specification are herein incorporated in their entirety by reference into the specification, to the same extent as if each individual publication, patent or patent application or GenBank Accession number was specifically and individually indicated to be incorporated herein by reference. In addition, citation or identification of any reference in this application shall not be construed as an admission that such reference is available as prior art to the present invention.

REFERENCES CITED BY NUMERALS IN THE APPLICATION

1. Toole, B. P. Hyaluronan and its binding proteins, the hyaladherins. Curr Opin Cell Biol, 2: 839-844, 1990.
2. Slevin, M., Krupinski, J., Kumar, S., and Gaffney, J. Angiogenic oligosaccharides of hyaluronan induce protein tyrosine kinase activity in endothelial cells and activate a cytoplasmic signal transduction pathway resulting in proliferation. Lab Invest, 78: 987-1003, 1998.
3. Stern, R. Devising a pathway for hyaluronan catabolism: are we there yet? Glycobiology, 13: 105R-115R, 2003.
4. Balazs, E. A., Hogberg, B., and Laurent, T. C. The biological activity of hyaluron sulfuric acid. Acta Physiol Scand, 23: 168-178, 1951.
5. Cobbin, L. B. and Dicker, S. E. Some characteristics of plasma and urine 'hyaluronidase'. J Physiol (Paris), 163: 168-174, 1962.
6. Toole, B. P. Hyaluronan: from extracellular glue to pericellular cue. Nat Rev Cancer, 4: 528-539, 2004.
7. Csoka, A. B., Frost, G. I., and Stern, R. The six hyaluronidase-like genes in the human and mouse genomes. Matrix Biol, 20: 499-508, 2001.
8. Afify, A. M., Stern, M., Guntenhoner, M., and Stern, R. Purification and characterization of human serum hyaluronidase. Arch Biochem Biophys, 305: 434-441, 1993.
9. Wei, M. H., Latif, F., Bader, S., Kashuba, V., Chen, J. Y., Duh, F. M., Sekido, Y., Lee, C. C., Geil, L., Kuzmin, I., Zabarovsky, E., Klein, G., Zbar, B., Minna, J. D., and Lerman, M. I. Construction of a 600-kilobase cosmid clone contig and generation of a transcriptional map surrounding the lung cancer tumor suppressor gene (TSG) locus on human chromosome 3p21.3: progress toward the isolation of a lung cancer TSG. Cancer Res, 56: 1487-1492, 1996.
10. Novak, U., Stylli, S. S., Kaye, A. H., and Lepperdinger, G. Hyaluronidase-2 overexpression accelerates intracerebral but not subcutaneous tumor formation of murine astrocytoma cells. Cancer Res, 59: 6246-6250, 1999.
11. Chang, N. S. Transforming growth factor-beta1 blocks the enhancement of tumor necrosis factor cytotoxicity by hyaluronidase Hyal-2 in L929 fibroblasts. BMC Cell Biol, 3: 8, 2002.
12. West, D. C., Hampson, I. N., Arnold, F., and Kumar, S. Angiogenesis induced by degradation products of hyaluronic acid. Science, 228: 1324-1326, 1985.
13. Tamakoshi, K., Kikkawa, F., Maeda, O., Suganuma, N., Yamagata, S., Yamagata, T., and Tomoda, Y. Hyaluronidase activity in gynaecological cancer tissues with different metastatic forms. Br J Cancer, 75: 1807-1811, 1997.
14. Jones, L., M J, G., J B, C., and G A, T. Hyaluronic acid secreted by mesothelial cells: a natural barrier to. Clin Exp Metastasis, 13: 373-380, 1995.
15. Carpenter, P. M. and Dao, A. V. The role of hyaluronan in mesothelium-induced motility of ovarian carcinoma cells. Anticancer Res, 23: 3985-3990, 2003.
16. Casey, R. C., Oegema, T. R., Jr., Skubitz, K. M., Pambuccian, S. E., Grindle, S. M., and Skubitz, A. P. Cell membrane glycosylation mediates the adhesion, migration, and invasion of ovarian carcinoma cells. Clin Exp Metastasis, 20: 143-152, 2003.
17. Lessan, K., Aguiar, D. J., Oegema, T., Siebenson, L., and Skubitz, A. P. CD44 and beta1 integrin mediate ovarian carcinoma cell adhesion to peritoneal mesothelial cells. Am J Pathol, 154: 1525-1537, 1999.
18. Gardner, M. J., Catterall, J. B., Jones, L. M., and Turner, G. A. Human ovarian tumour cells can bind hyaluronic acid via membrane CD44: a possible step in peritoneal metastasis. Clin Exp Metastasis, 14: 325-334, 1996.
19. Stern, M. and Stern, R. An ELISA-like assay for hyaluronidase and hyaluronidase inhibitors. Matrix, 12: 397-403, 1992.
20. Frost, G. I. and Stern, R. A microtiter-based assay for hyaluronidase activity not requiring specialized reagents. Anal Biochem, 251: 263-269, 1997.
21. Vercruysse, K. P., Lauwers, A. R., and Demeester, J. M. Kinetic investigation of the degradation of hyaluronan by hyaluronidase using gel permeation chromatography. J Chromatogr B Biomed Appl, 656: 179-190, 1994.
22. Takahashi, T., Ikegami-Kawai, M., Okuda, R., and Suzuki, K. A fluorimetric Morgan-Elson assay method for hyaluronidase activity. Anal Biochem, 322: 257-263, 2003.
23. Cramer, J. A. and Bailey, L. C. A reversed-phase ion-pair high-performance liquid chromatography method for bovine testicular hyaluronidase digests using postcolumn derivatization with 2-cyanoacetamide and ultraviolet detection. Anal Biochem, 196: 183-191, 1991.
24. Gouin, S. and Winnik, F. M. Quantitative assays of the amount of diethylenetriaminepentaacetic acid conjugated to water-soluble polymers using isothermal titration calorimetry and colorimetry. Bioconjug Chem, 12: 372-377, 2001.
25. Grabbe, K. J., Shelton, J. M., Richardson, J. A., Hascall, V. C., and Mahendroo, M. S. Regulation of hyaluronan expression during cervical ripening. Glycobiology, 2004.
26. Rai, S. K., Duh, F. M., Vigdorovich, V., Danilkovitch-Miagkova, A., Lerman, M. I., and Miller, A. D. Candidate tumor suppressor HYAL2 is a glycosylphosphatidylinositol (GPI)-anchored cell-surface receptor for jaagsiekte sheep retrovirus, the envelope protein of which mediates oncogenic transformation. Proc Natl Acad Sci USA, 98: 4443-4448, 2001.
27. Bogdanov, A., Jr., Matuszewski, L., Bremer, C., Petrovsky, A., and Weissleder, R. Oligomerization of paramagnetic substrates result in signal amplification and can be used for MR imaging of molecular targets. Mol Imaging, 1: 16-23, 2002.
28. Louie, A. Y., Huber, M. M., Ahrens, E. T., Rothbacher, U., Moats, R., Jacobs, R. E., Fraser, S. E., and Meade, T. J. In vivo visualization of gene expression using magnetic resonance imaging. Nat Biotechnol, 18: 321-325, 2000.
29. Zhao, M., Josephson, L., Tang, Y., and Weissleder, R. Magnetic sensors for protease assays. Angew Chem Int Ed Engl, 42: 1375-1378, 2003.
30. Alfke, H., Stoppler, H., Nocken, F., Heverhagen, J. T., Kleb, B., Czubayko, F., and Klose, K. J. In vitro MR imaging of regulated gene expression. Radiology, 228: 488-492, 2003.
31. Bremer, C. and Weissleder, R. In vivo imaging of gene expression. Acad Radiol, 8: 15-23, 2001.
32. Hogemann, D., Ntziachristos, V., Josephson, L., and Weissleder, R. High throughput magnetic resonance imaging for evaluating targeted nanoparticle probes. Bioconjug Chem, 13: 116-121, 2002.
33. Cohen, B., Dafni, H., Meir, G., Harmelin, A., and Neeman, M. Ferritin as an endogenous MRI reporter for Molecular Imaging of Gene Expression. Neoplasia In Press, 2004.

What is claimed is:

1. A composition-of-matter comprising a chelator moiety-hyaluronan complex bound to a solid support, wherein said chelator moiety is selected from the group consisting of 1,4,7,10-tetraazacyclodo-decane-N,N',N", N'''-tetraacetic acid; 1,4,7,10-tetraaza-cyclododecane-N,N',N"-triacetic acid; 1,4,7-tris (carboxymethyl)-10-(2'-hydroxypropyl)-1,4,7,10-tetraazocyclodecane; 1,4,7-triazacyclonane-N,N',N"-triacetic acid; 1,4,8,11-tetraazacyclotetra-decane-N,N',N",N'"-tetraacetic acid; diethylenetriamine-pentaacetic acid (DTPA); ethylenedicysteine; bis(aminoethanethiol)carboxylic acid; triethylenetetraamine-hexaacetic acid; ethylenediamine-tetraacetic acid (EDTA); 1,2-diaminocyclohexane-N,N,N',N'-tetraacetic acid; N-(hydroxy-ethyl)ethylenediaminetriacetic acid; nitrilotriacetic acid; and ethylene-bis(oxyethylene-nitrilo)tetraacetic acid; wherein said solid support is a bead.

2. The composition-of-matter of claim 1, wherein said chelator moiety-hyaluronan complex is cleavable by hyaluronidase.

3. The composition-of-matter of claim 1, wherein said bead is an avidin-covered bead.

4. The composition-of-matter of claim 3, wherein said chelator moiety-hyaluronan complex is bound to said avidin-covered bead via a biotin linker.

5. The composition-of-matter of claim 4, wherein said biotin linker is biotinamidopentylamine.

6. The composition-of-matter of claim 1, wherein said chelator moiety is diethylenetriamine-pentaacetic acid (DTPA).

7. The composition-of-matter of claim 1, further comprising a metal ion or atom being attached to said chelator moiety.

8. The composition-of-matter of claim 7, wherein said metal ion or atom is a paramagnetic metal ion or atom.

9. The composition-of-matter of claim 7, wherein said metal ion or atom is a supermagnetic metal ion or atom.

10. The composition-of-matter of claim 7, wherein said metal ion or atom is a transition metal ion or atom.

11. The composition-of-matter of claim 7, wherein said metal ion or atom is a lanthanide ion or atom.

12. The composition-of-matter of claim 7, wherein said metal ion or atom is selected from the group consisting of Eu, Ho, Dy, Mn, Gd, Cr, Hf, La, Yb, Tc and In.

13. The composition-of-matter of claim 7, wherein said metal ion or atom is Gd.

14. A method of imaging activity of hyaluronidase in situ, the method comprising:
contacting a biological tissue with a composition-of-matter which comprises a chelator moiety-hyaluronan complex bound to a solid support, said complex being an indicator designed for detecting activity of hyaluronidase, and said chelator moiety is selected from the group consisting of 1,4,7,10-tetraazacyclodo-decane-N,N',N",N'"-tetraacetic acid; 1,4,7,10-tetraaza-cyclododecane-N,N',N"-triacetic acid; 1,4,7-tris(carboxymethyl)-10-(2'-hydroxypropyl)-1,4,7,10-tetraazocyclodecane; 1,4,7-triazacyclonane-N,N',N"-triacetic acid; 1,4,8,11-tetraazacyclotetra-decane-N,N',N",N'"-tetraacetic acid; diethylenetriamine-pentancetic acid (DTPA); ethylenedicysteine; bis(aminoethanethiol)carboxylic acid; triethylenetetraamine-hexaacetic acid; ethylenediamine-tetraacetic acid (EDTA); 1,2-diaminocyclohexane-N,N,N',N'-tetraacetic acid; N-(hydroxy-ethyl)ethylenediaminetriacetic acid; nitrilotriacetic acid; and ethylene-bis(oxyethylene-nitrilo)tetraacetic acid; wherein said solid support is a bead; and imaging the signal generated by said indicator, thereby imaging activity of hyaluronidase in the biological sample in situ.

15. The method of claim 14, wherein said chelator moiety-hyaluronan complex is cleavable by hyaluronidase.

16. The method of claim 14 wherein said bead is an avidin-covered bead.

17. The method of claim 16, wherein said chelator moiety-hyaluronan complex is bound to said avidin-covered bead via a biotin linker.

18. The method of claim 17, wherein said biotin linker is biotinamidopentylamine.

19. The method of claim 14, wherein said chelator moiety is diethylenetriamine-pentaacetic acid (DTPA).

20. The method of claim 14, wherein said indicator further includes a metal ion or atom being attached to said chelator moiety.

21. The method of claim 20, wherein said metal ion or atom is a paramagnetic metal ion or atom.

22. The method of claim 20, wherein said metal ion or atom is a supermagnetic metal ion or atom.

23. The method of claim 20, wherein said metal ion or atom is a transition metal ion or atom.

24. The method of claim 20, wherein said metal ion or atom is a lanthanide ion or atom.

25. The method of claim 20, wherein said metal ion or atom is selected from the group consisting of Eu, Ho, Dy, Mn, Gd, Cr, Hf, La, Yb, Tc and In.

26. The method of claim 20, wherein said metal ion or atom is Gd.

* * * * *

SEQUENCE LISTING

<160> NUMBER OF SEQ ID NOS: 4

<210> SEQ ID NO 1
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 1
gctcaagccc acagcaccac                                              20

<210> SEQ ID NO 2
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 2
cagtgtctcc agcatgaact gc                                           22

<210> SEQ ID NO 3
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 3
caccgtctgg aatgcaaaca                                              20

<210> SEQ ID NO 4
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 4
gttggctacc acatcgaaga ca                                           22